United States Patent
Gibson

(10) Patent No.: US 10,070,830 B2
(45) Date of Patent: *Sep. 11, 2018

(54) X-RAY IMAGING APPARATUS AND METHODS

(71) Applicant: IBEX Innovations Ltd., Sedgefield Durham (GB)

(72) Inventor: Gary Gibson, Sedgefield Durham (GB)

(73) Assignee: IBEX Innovations, Ltd., Sedgefield, Stockton-on-Tees (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/891,463

(22) PCT Filed: May 16, 2014

(86) PCT No.: PCT/GB2014/051524
§ 371 (c)(1),
(2) Date: Nov. 16, 2015

(87) PCT Pub. No.: WO2014/184588
PCT Pub. Date: Nov. 20, 2014

(65) Prior Publication Data
US 2016/0157794 A1    Jun. 9, 2016

(30) Foreign Application Priority Data
May 16, 2013   (GB) .................................. 1308876.0

(51) Int. Cl.
*G09G 3/30*    (2006.01)
*A61B 6/00*    (2006.01)
(Continued)

(52) U.S. Cl.
CPC ............ *A61B 6/4035* (2013.01); *A61B 6/032* (2013.01); *A61B 6/06* (2013.01); *A61B 6/4233* (2013.01);
(Continued)

(58) Field of Classification Search
CPC ........................... G01N 23/203; G01N 23/005
See application file for complete search history.

(56) References Cited

U.S. PATENT DOCUMENTS

| | | |
|---|---|---|
| 3,950,613 A | 4/1976 | Macovski |
| 3,965,358 A | 6/1976 | Macovski |

(Continued)

FOREIGN PATENT DOCUMENTS

| | | |
|---|---|---|
| DE | 102007058447 A1 | 6/2009 |
| EP | 1063538 A2 | 6/2000 |

(Continued)

OTHER PUBLICATIONS

PCT International Search Report, Application No. PCT/GB2014/051524, dated Sep. 26, 2014.
(Continued)

*Primary Examiner* — Don Wong
(74) *Attorney, Agent, or Firm* — MacMillan, Sobanski & Todd, LLC

(57) ABSTRACT

An x-ray/gamma ray imaging apparatus includes a pixilated x-ray/gamma ray detector (3) including a member configured to detect incident x-ray/gamma ray wavelength photons, a position for a body under test (2), an x-ray or gamma ray source (1), and a structure configured to perturb the energy spectrum (6), each lying on a common axis. The source is arranged to direct an x-ray gamma ray energy spectrum along the common axis to impinge upon a structure configured to perturb the x-ray energy spectrum and a positioned body/object under test. The structure and the position for the body under test lie between the source and the detector member, and the structure includes at least three adjacent regions, each region different to immediately adjacent regions and configured to perturb the x-ray energy (Continued)

spectrum differently. Detected photons are subject to a random noise reduction algorithm.

41 Claims, 9 Drawing Sheets

(51) Int. Cl.
    *G21K 1/10*     (2006.01)
    *H05G 1/00*     (2006.01)
    *G01T 1/20*     (2006.01)
    *A61B 6/03*     (2006.01)
    *A61B 6/06*     (2006.01)

(52) U.S. Cl.
    CPC .......... *A61B 6/4258* (2013.01); *A61B 6/4275* (2013.01); *A61B 6/5258* (2013.01); *G01T 1/20* (2013.01); *G21K 1/10* (2013.01); *H05G 1/00* (2013.01)

(56) References Cited

U.S. PATENT DOCUMENTS

| | | | |
|---|---|---|---|
| 5,841,835 A * | 11/1998 | Aufrichtig | A61B 6/583 378/204 |
| 6,231,231 B1 * | 5/2001 | Farrokhnia | A61B 6/583 378/204 |
| 6,674,835 B2 * | 1/2004 | Kaufhold | A61B 5/4869 378/207 |
| 6,816,571 B2 * | 11/2004 | Bijjani | G01N 23/046 378/57 |
| 7,200,201 B2 | 4/2007 | Unger et al. | |
| 7,382,853 B2 | 6/2008 | Arenson et al. | |
| 8,155,729 B1 | 4/2012 | Hsieh et al. | |
| 8,199,875 B2 | 6/2012 | Chandra et al. | |
| 8,243,875 B2 | 8/2012 | Xu et al. | |
| 8,311,182 B2 | 11/2012 | Chandra et al. | |
| 8,363,779 B2 | 1/2013 | Chandra et al. | |
| 8,378,310 B2 | 2/2013 | Bornefalk et al. | |
| 8,406,373 B2 | 3/2013 | Graham et al. | |

FOREIGN PATENT DOCUMENTS

| | | |
|---|---|---|
| WO | 2004054329 A2 | 6/2004 |
| WO | 2006044692 A2 | 4/2006 |
| WO | 2008068690 A2 | 6/2008 |
| WO | 2008142446 A2 | 11/2008 |
| WO | 2009125211 A1 | 10/2009 |
| WO | 2009130492 A1 | 10/2009 |
| WO | 2010136790 A1 | 12/2010 |
| WO | 2011110862 A1 | 9/2011 |
| WO | 2012063169 A1 | 5/2012 |

OTHER PUBLICATIONS

PCT International Search Report, Application No. PCT/GB2014/051506, dated Sep. 4, 2014.
PCT International Search Report, Application No. PCT/GB2014/051525, dated Sep. 9, 2014.

* cited by examiner

FIGURE 5
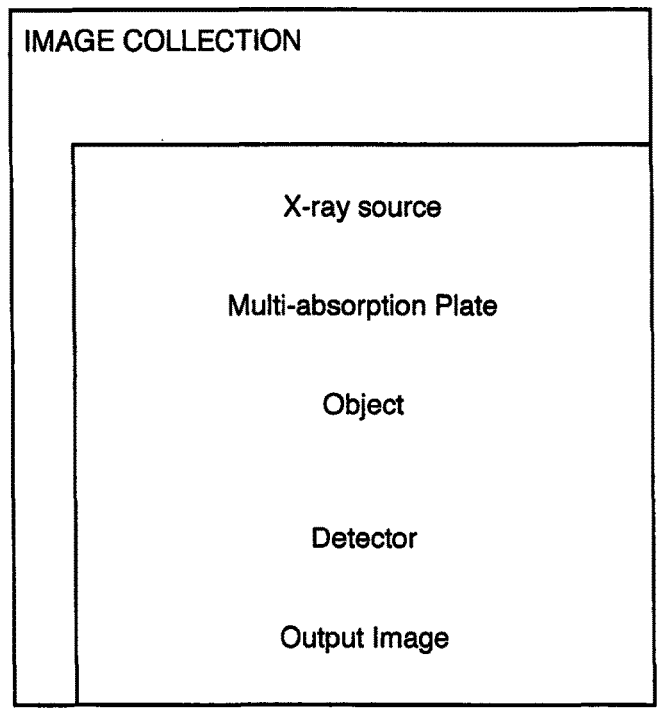
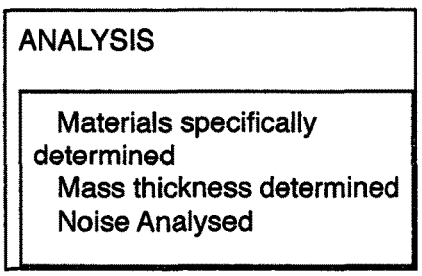
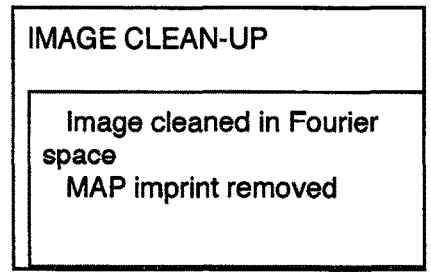
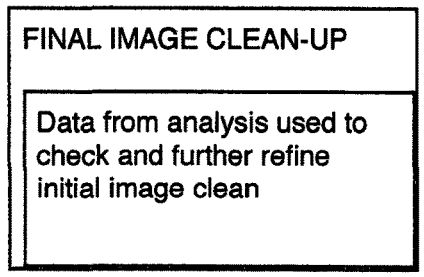

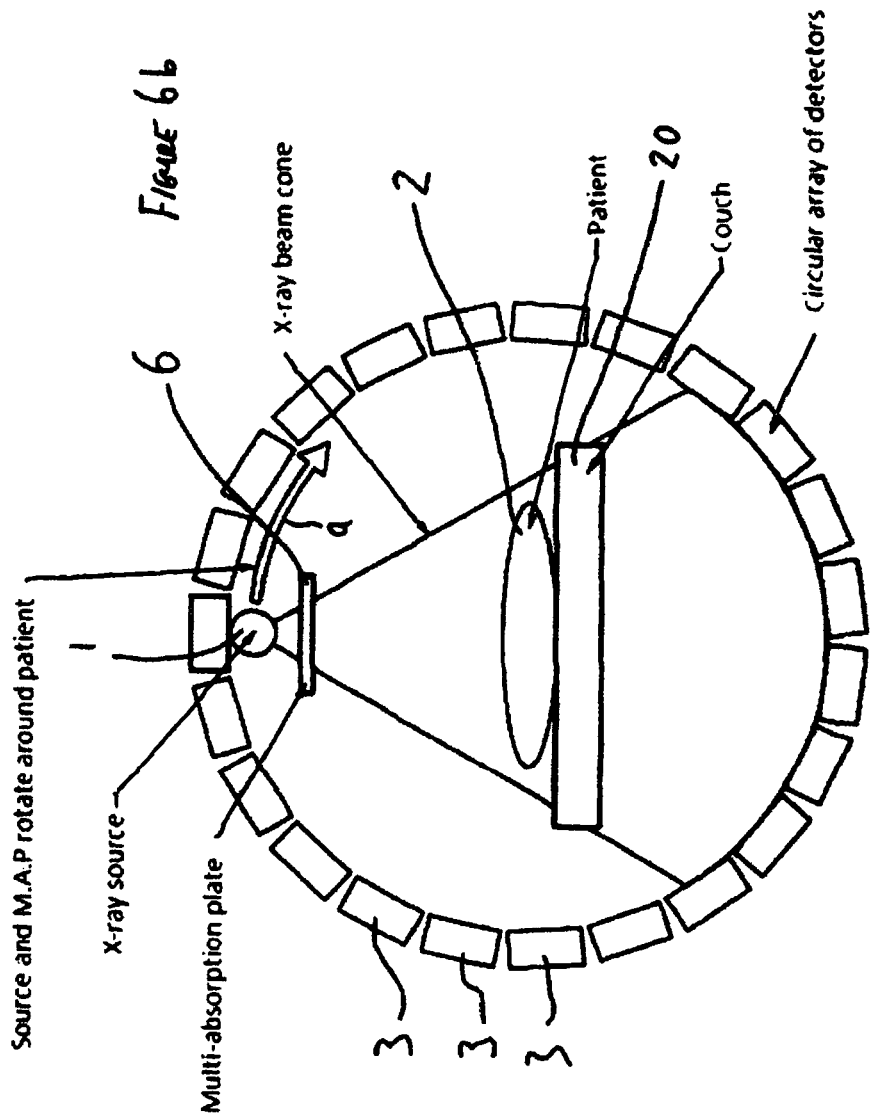

X-RAY IMAGING APPARATUS AND METHODS

CROSS-REFERENCE TO RELATED APPLICATIONS

This application is the National Phase of International Application PCT/GB2014/051524 filed May 16, 2014, which designated the U.S. That International Application was published in English under PCT Article 21(2) on Nov. 20, 2014 as International Publication Number WO 2014/184588A1. PCT/GB2014/051524 claims priority to U.K. Application No. 1308876.0 filed May 16, 2013. Thus, the subject nonprovisional application also claims priority to U.K. Application No. 1308876.0 filed May 16, 2013. The disclosures of both applications are disclosure of that application is incorporated herein by reference.

FIELD OF THE INVENTION

The invention relates to x-ray imaging apparatus and methods, and in particular to x-ray imaging apparatus and methods for use with materials sensitive to x-ray energy.

BACKGROUND OF THE INVENTION

X-ray imaging apparatus is widely used in medical and veterinary applications in order to obtain images of tissues hidden from view with the naked eye. It is widely understood that whilst x-ray imaging can be of assistance in diagnosis, subjecting a patient to x-rays of itself carries risks. In the case of computed tomography (CT) scanning equipment, the risk posed to patients is very significant. Data published by the UK Health Protection Agency shows that in CT scanning the x-ray energy to which the patient is subjected is so high that for every one thousand people having a CT scan, one person will die as a result of the scan. In some jurisdictions before a patient may receive a CT scan it is a requirement that a consultant give an opinion that the risk to the patient's life from the condition that is being investigated is greater than the risk to the patient's life from having the CT scan.

It would therefore be very desirable in an x-ray imaging apparatus, and in particular in CT scanners, to reduce the x-ray dose received by the patient.

It is known that x-rays having lower energies are more harmful to the patient than higher energy x-rays. This is because the lower energy x-rays are absorbed more readily by the tissues of the body, whereas the higher energy x-rays tend to pass through the tissues of the body with a lower rate of absorption.

It is known that lower energy x-rays may be removed from an x-ray spectrum in a process known as beam hardening. This would reduce the effective dose to the patient. However, the contrast seen by the x-ray detector would be reduced and hence the image quality would be reduced.

The issue of dose reduction has been addressed, particularly in relation to CT scanners where the problem of over exposure to x-rays is most severe.

For example, blocking filters may be used as exemplified in U.S. Pat. No. 8,243,875, in which Xu describes a computer controlled aperture in front of the x-ray source to constrain the x-ray beam angle so that only those areas of interest in an object under examination are illuminated by the x-rays.

Another approach involves active feedback of x-ray attenuation with reduction of dose to minimal needed signal to noise, as exemplified in U.S. Pat. No. 8,406,373, in which Graham describes equipment that would allow variation in X-ray flux using a modulator at different parts of an image to give high signal to noise and corresponding high dose in areas of an image where detail is vital and a lower signal to noise and hence dose in other areas of the image where detail is less important.

Another approach to dose reduction is to combine x-ray imaging with other techniques. For example, in U.S. Pat. No. 8,155,729 Hsieh describes apparatus that gathers x-ray and ultrasound data in cardiac imaging and combines the data. This is said to reduce the number of slices needed in the CT scan, thereby reducing dose.

Another approach involves the mathematical treatment of data. In U.S. Pat. No. 8,363,779 and U.S. Pat. No. 8,199,875 Chandra describes inventions which allow the seamless integration of datasets that are obtained from x-ray beams set at two different energies. The integration of the datasets enhances contrast and gives material specificity. This method has to be timed very carefully so the datasets are collected in such a way that does not increase the dose given to the patient. They are at best dose neutral compared to a standard instrument, but give additional information.

Yet another approach involves improving the component equipment. In U.S. Pat. No. 8,378,310 Bournefalk describes a method to accommodate pulse pile-up in photon counting detectors which improves the signal quality of the detector thus allowing for lower doses to be used for patients when pulse pile-up is present. In U.S. Pat. No. 7,200,201 Unger describes a method of using collimation to reduce the amount of scattered radiation that enters a detector, hence improving the contrast obtained and allowing for lower doses.

Whilst the above described devices may reduce x-ray dose it is understood that the dose reduction levels are marginal. It would be desirable to provide apparatus capable of making significant reductions in x-ray dose without compromising the results of the x-ray imaging.

The main area of use of such an x-ray apparatus would be in human and animal medicine. However, there are other areas of use, in fact such an apparatus would have utility in analysing any body or substance that is sensitive damage by x-rays, such as plant material and polymers for example.

SUMMARY OF THE INVENTION

According to a first aspect of the invention there is provided x-ray imaging apparatus, the apparatus including an x-ray or gamma ray detector comprising a pixilated member configured to detect incident x-ray/gamma ray wavelength photons a position for a body/object under test, an x-ray or gamma ray source, and a structure configured to perturb the radiation energy spectrum, each lying on a common axis, wherein the source is arranged to direct an x-ray/gamma ray energy spectrum along the common axis, the structure configured to perturb the energy spectrum, and positioned body under test, wherein said structure and the position for the body under test lie between the x-ray source and the pixilated member and wherein the said structure lies either between the x-ray source and the position for the body under test or between the position for the body under test and the detector each intersecting the common axis, wherein the said structure comprises at least three adjacent regions, each region different to immediately adjacent regions and configured to perturb the x-ray energy spectrum differently.

The structure may comprise repeating arrays each array comprising at least three adjacent regions, each region different to immediately adjacent regions and configured to perturb the x-ray energy spectrum differently.

The x-ray imaging apparatus may include a collimator configured to collimate x-ray wavelength photons emitted by the x-ray source, and each array of the structure of repeating arrays may be aligned with beam of x-ray energy produced by the collimator.

The member configured to detect incident x-ray/gamma ray radiation may be an indirect detector and include a scintillator.

Other detectors include: Silicon diode detectors, lithium drifted silicon detectors, high purity Germaium detectors HPGe, Cd based detectors—CdTe, CdZnTe, CdMnTe and others, proportional counters, gas filled detectors.

According to an aspect of the invention there is provided an x-ray/gamma ray imaging apparatus as specified in Claim 1.

Preferably, the said structure lies between the x-ray source and the position for the body under test each intersecting the common axis.

Preferably, the said structure lies between the position for the body under test and the detector each intersecting the common axis.

Preferably, one of the regions is an aperture.

Preferably, the number of pixels in the detector member is greater than or equal to the number of regions in the structure.

The apparatus may further comprise data recording means configured to record the detected incident x-ray/gamma ray wavelength photons for individual pixels and/or groups of pixels. Differences between the outputs of pixels of the detector and information stored in the database may be recorded in the data recording means.

Preferably, the image processing software is configured to remove the effect of the structure on the detected x-ray/gamma ray photons.

Preferably, the noise reduction algorithm is a random noise reduction algorithm.

Preferably, the noise reduction algorithm compares the difference in outputs of adjacent pixels of the detector with differences between outputs of adjacent pixels for identified database entries and amends the outputs of the adjacent pixels of the detector such that the differences in those outputs resembles more closely the differences between outputs of adjacent pixels for identified database entries that are similar to the outputs of adjacent pixels of the detector.

Preferably, the image processing software is configured such that amendment of the outputs of pixels in a group of pixels associated with a region of the structure is common to the output of each pixel in the group.

Preferably, the image processing software is configured such that the extent to which the outputs are amended to resemble more closely the difference between outputs of adjacent pixels for the identified database entries that are similar to the outputs of adjacent pixels of the detector is controllable.

Preferably, the image processing software is configured to select the extent of amendment according to the degree of certainty that a group of pixels represent the same material, and wherein the greater the certainty, the greater the amendment of the outputs adjacent pixels of the detector may be.

Preferably, the noise reduction algorithm identifies information in the database that most closely resembles outputs of pixels of the detectors and replaces the outputs of pixels with the identified information in the database.

Preferably, the outputs of pixels in a group of pixels associated with a region of the structure are replaced with the same identified information.

Preferably, the image processing software is configured to provide an output of a characteristic associated with the detection of a certain material type and/or material thickness.

According to another aspect of the invention there is provided a medical device as specified in Claim 18. Preferably, the device comprises a plurality of detectors and more preferably, the plurality of detectors is mounted for rotation about the patient support.

According to another aspect of the invention there is provided an image analysis process as specified in Claim 21.

The image analysis process may comprise the step of recording the detected incident x-ray/gamma ray wavelength photons for individual pixels and/or groups of pixels in the data recording means.

The image analysis process may comprise the step of removing the effect of the structure on the detected x-ray/gamma ray photons.

The image analysis process may include the step of grouping together pixels having similar outputs.

The image analysis process may comprise the step of assigning the same output to all pixels in a group of pixels.

The image analysis process may comprise the step of recording differences between the outputs of pixels of the detector and information stored in the database in the data recording means.

The image analysis process, the step of executing the algorithm to determine the material type and/or thickness of a material preferably including comparing the actual intensity detected at a pixel or assigned to a group of pixels with actual intensities recorded in the database.

The image analysis process, the algorithm preferably comprising the further step of comparing differences between the averages of detected actual intensities related to different regions of the structure with the differences between the averages of actual intensities related to the same different regions of the structure in the database.

The image analysis process, the algorithm preferably comprising the further step of comparing the second and third moments of the transmission space of the detected intensities related to different regions of the structure with the second and third moments of the transmission space for intensities stored in the database and related to the same different regions of the structure.

The image analysis process, the algorithm preferably including the further step of issuing a probability indicating that the body under test is the same as a known material type and/or thickness as stored in the database.

The image analysis process, the image processing software preferably executing the noise reduction algorithm.

The image analysis process, the noise reduction algorithm preferably configured to suppress the variance in pixel to pixel differences in the actual detected intensity and pixel to pixel differences in the database for the identified material.

The image analysis process, the degree of variance suppression preferably controlled in relation to the issued probability of the body under test being a known material type and/or thickness and wherein greater the probability the greater the suppression of the variance.

The image analysis process, the noise reduction algorithm preferably comparing the difference in outputs of adjacent pixels of the detector with differences between outputs of adjacent pixels in the database and amends the outputs of the adjacent pixels of the detector such that the differences in those outputs resembles more closely the differences between outputs of adjacent pixels in the database.

The image analysis process image processing software preferably making a common amendment to the outputs of pixels in a group of pixels associated with a region of the structure.

The image analysis process the image processing software preferably controls the extent to which the outputs are amended to resemble more closely the difference between outputs of adjacent pixels in the database.

The image analysis process, preferably comprising the step of controlling the extent of amendment according to the degree of certainty that a group of pixels represent the same material, and wherein the greater the certainty, the greater the amendment of the outputs adjacent pixels of the detector may be.

The image analysis process, the noise reduction algorithm preferably identifying information in the database that most closely resembles outputs of pixels of the detectors and replaces the outputs of pixels with the identified information in the database.

The image analysis process, preferably comprising the step of replacing the outputs of pixels in a group of pixels associated with a region of the structure with the same identified information.

The image analysis process, preferably comprising the additional step of providing an output indicating the probability of one or more characteristics being associated with the identified the material type and/or material thickness.

The image analysis process, the characteristic preferably being indicative of a medical condition.

The output of the apparatus and/or image analysis process is preferably an image or data from which an image may be generated, that image or data having the noise therein reduced.

BRIEF DESCRIPTION OF THE DRAWINGS

In the Drawings, which illustrate preferred embodiments of x-ray imaging apparatus according to the invention:

FIG. 5 is a flow diagram illustrating operation of x-ray imaging apparatus according to the invention;

FIG. 6b is an end view of the CT scanning x-ray apparatus illustrated in FIG. 6a FIG. 7 illustrates components of the apparatus of the invention and a graph of average detected intensity v time;

DETAILED DESCRIPTION OF THE PREFERRED EMBODIMENTS

Figure 1:
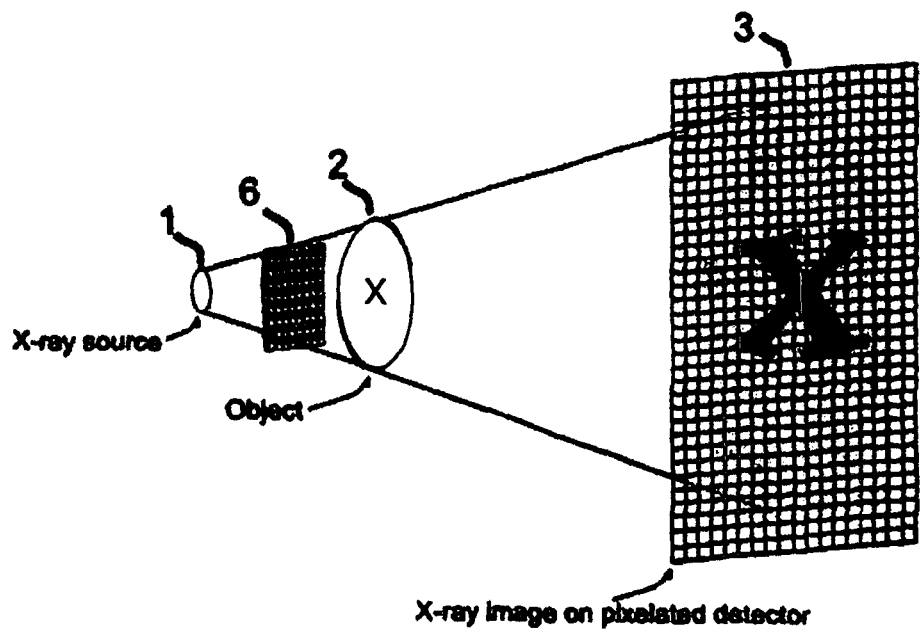
FIG. 1 is a schematic representation of an x-ray detector of the invention.

FIG. 1 illustrates the basic components of an x-ray detector according to the invention. The detector comprises an x-ray source 1, a position for an object 2 under test, a multi-absorption plate 6 in which different regions of the plate have different x-ray absorption capabilities, and which may be formed of tungsten for example, and an x-ray camera 3 in the form of a scintillator. The multi-absorption plate is situated between the x-ray source 1 and the object 2. The different regions of the plate 6 may have different absorption capabilities by virtue of the regions having different thicknesses, or the interference plate may have uniform thickness, with the material difference between adjacent regions being provided by forming the individual regions of the interference plate of different materials or a combination of these alternatives.

The interference plate may comprise a substrate with the individual regions formed on or in the substrate. The individual regions may be formed in the base layer by etching or even machining the substrate.

The effect of the multi-absorption plate 6 is to attenuate the signal emanating from the source 1 and stamps on to the image detected by the x-ray camera 3 the structure of the multi-absorption plate 6.

Stamping the structure of the multi-absorption plate on to the image hardens the x-ray spectrum reaching the object under test, which has two effects. First, as the x-rays pass through the multi-absorption plate they are selectively absorbed, each area of different material property (thickness for example) absorbing x-rays differently. The overall effect is to reduce in x-ray flux reaching the object 2 and/or to increase the average energy of the beam, thereby reducing the dose received by the object.

Conventional wisdom in this area would consider hardening of the x-ray energy spectrum to be unfavourable as the contrast seen by the detector plate is reduced and image quality compromised. Whilst this is correct in respect of hardening that is applied consistently across an energy spectrum, for example by passing the x-ray beam through a plate of uniform thickness, the same problem does not arise with a multi-absorption plate.

The structure perturbs the x-ray energy spectrum differently at different regions. This induces contrast within the x-ray energy spectrum before the x-ray energy impinges upon the body under test. Small differences between materials, such as soft tissues, can be difficult to discern. Inducing even small differences within the x-ray energy spectrum can assist in distinguishing one material from another because the different materials may have different effects on the x-ray spectra having different energies.

The x-ray hardening resulting from passing the x-ray beam through the multi-absorption plate reduces the x-ray count by approximately 50%.

The structure that is introduced into the X-ray beam by the multi-absorption plate allows the detected image to be analysed and the contrast loss recovered. In essence, the effect of the structure on the x-ray beam can be measured without any object under test present and the effect of the structure when the apparatus is used to take an x-ray of a patient for example, can be removed from the data recorded by the x-ray detector, because the effect of the structure is known.

Second, and more significantly, it is possible to use information known about the effect of the multi-absorption plate on the x-ray beam to recover a better image when the signal to noise ratio is worse. That is, the use of the multi-absorption plate and subsequent mathematical processing gives the apparatus of the invention a greater tolerance to noise than x-ray imaging equipment presently known in the art. It is therefore possible to obtain an image with the same quality with a significantly lower x-ray flux resulting in fewer photons striking the object. Conversely, a significantly higher quality image can be achieved at the same x-ray flux and a moderately improved image at a moderately reduced x-ray flux, the x-ray flux being indicative of the dose received by a patient. The calculations below demonstrate that it is possible to reduce the error by at least 50%, which in turn means that the x-ray dose may be reduced by a factor of 4.

Figure 7:
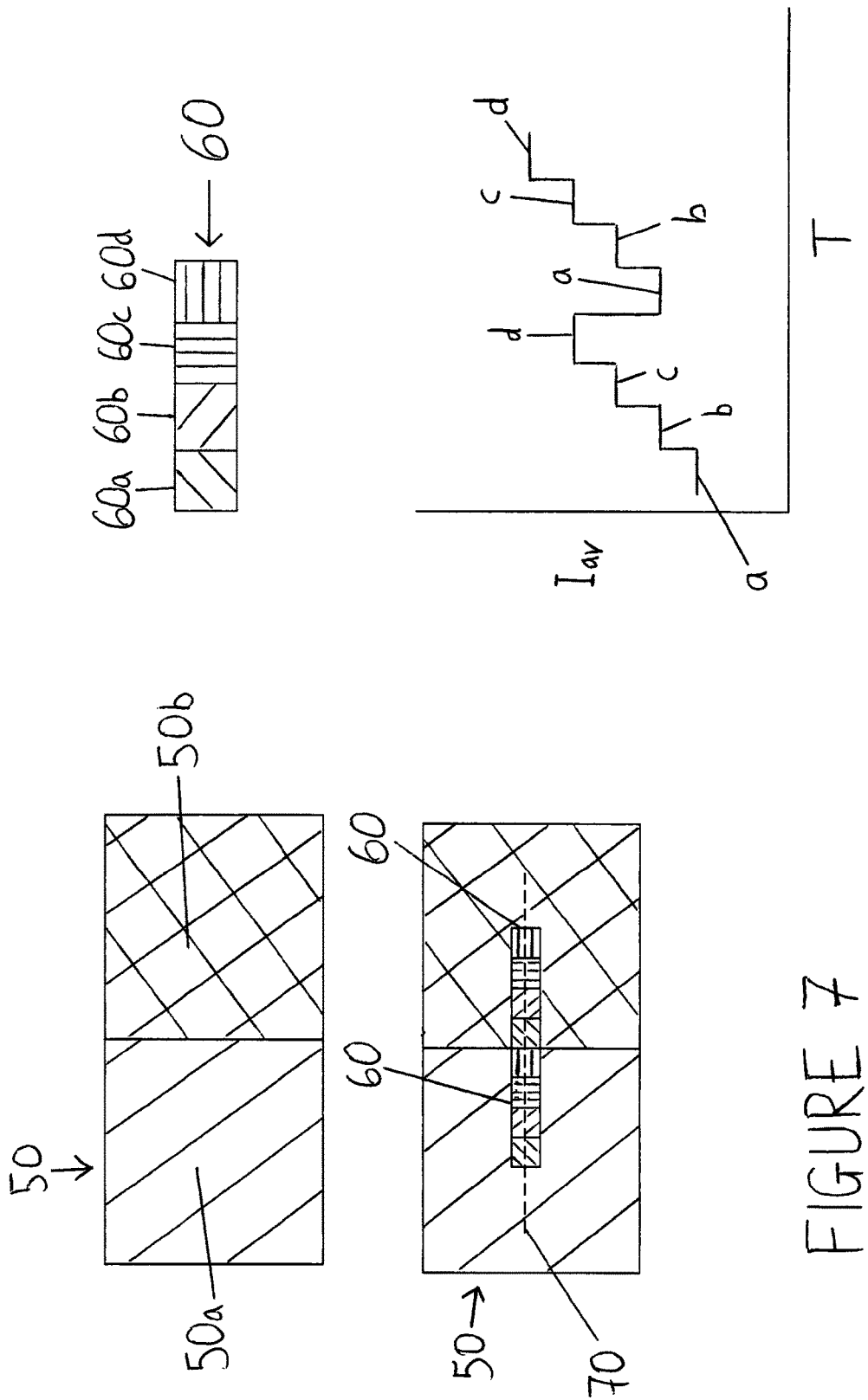

It is known that for a given x-ray source, the intensity measured at a particular pixel of the same detector will vary over short periods of time, but that the average intensity measured at the pixel will be essentially constant. This is illustrated in FIG. 7, which shows the random variation in measured intensity over time and the average. Hence, if an object under test could be tested for a long period of time, short term variations in intensity would not be relevant. However, in the case of imaging biological tissues or other materials that may be damaged by exposure to x-rays, periods of exposure must be kept to the minimum possible.

The multi-absorption plate can be exposed to x-rays for very long periods of time, as can other materials where any sensitivity to x-rays is not of great consequence. Hence, for a particular apparatus, the long term average intensity associated with a particular region of the multi-absorption plate may be ascertained. This information can be associated with particular pixels or groups of pixels of the detector and used in the processing of a subsequently captured image. For example, the intensity signal detected at a particular pixel during imaging of an object may be compared with the expected intensity signal for that pixel and modified accordingly.

If a single two by two array having regions 1 to 4 is considered, then the true intensity of the x-ray source can be established by long term measurement of the individual regions. However, a quick measurement also gives an estimate of the intensity at that particular time but the intensity is distorted by noise.

The relative intensity change from area 1-4 can be established by long term testing of the structure as discussed above. When the apparatus is used to take an x-ray image of a body, noise will add errors into each individual area, but that additional noise will be unique to each area. Therefore, as the true relationship between adjacent regions of the array is known, the change induced by the noise can be decoupled. The absolute value of the intensity at any region of the array however may change and may be a true change due to the effect of the body under test on the x-ray, so what is being compared are relative changes from area to area. With the noise component separated, noise distortion can be removed algebraically from the measured value hence cleaning the data.

The multi-absorption plate therefore allows the signal to be reduced as the corresponding decrease in signal to noise ratio can be recovered. Hence, the x-ray flux may be turned down and/or the average beam energy increased and the same quality of image obtained. Calculations show that it is possible to reduce the error by at least 50%, which means that it is possible to reduce the dose by a factor of four without compromising image quality.

Mathematical Proof of Benefit of Multi-Absorption Plate

A material of known thickness may be identified using the exponential attenuation law.

The exponential attenuation law allows a material X and its thickness t to be identified, as follows:

$$T = \frac{I_X}{I_0} = \exp(-\mu_X t_X)$$

Where:
T=transmission
I=intensity
μ=mass attenuation coefficient
t=mass thickness If information on the intensity is only taken at one energy then the equation can never be solved uniquely for both thickness $t_X$ and attenuation coefficient $\mu_X$.

A solution to this problem is to introduce a material between the x-ray source and the material under test which changes the intensity incident on the material under test. For example if a copper foil of known thickness $t_{Cu}$ and that known transmission $T_{Cu}$ then:

$$T_{Cu} = \frac{I_{Cu}}{I_0} = \exp(-\mu_{Cu} t_{Cu})$$

Then if we observe an unknown material X using an x-ray that has passed through the Cu foil, i.e. the Cu response has been stamped onto that material then we can write:

$$T_{Cu+X} = \frac{I_{Cu+X}}{I_0} = \exp(-\mu_{Cu+X} t_{Cu+X})$$

We have that $t_{Cu+X}=t_{Cu}+t_X$ and $\mu_{Cu+X}$ is a linear combination of $\mu_{Cu}$ and $\mu_X$. Since $t_{Cu+X}=t_{Cu}+t_X$, we then have:

$$\frac{1}{\mu_{Cu+X}}\ln(T_{Cu+X}) = \frac{1}{\mu_X}\ln(T_X)\frac{1}{\mu_{Cu}}\ln(T_{Cu})$$

It's easy to see that, if we observe $T_{Cu+X}$, $T_{Cu}$, $T_X$, $\mu_X$ and $\mu_{Cu}$, we can estimate $\mu_{Cu+X}$; and if estimate this attenuation coefficient accurately, we can also estimate the thickness $t_{Cu+X}$ and consequently $t_X$.

If the assumption is made that $t_{Cu+X}=t_{Cu}+t_X$ and that $\ln(T_{Cu+X})$ is a linear combination of $\ln(T_X)$ and $\ln(T_{Cu})$ then the signal given by the material X by projecting it in linearly independent spaces created by the open beam and different copper foils can be decomposed. In the same way that light can be decomposed using different filters in a camera, i.e. red, green, blue and white filters, to create the RGB colour space, we can decompose the x-ray signal using linearly independent filters. By doing so it is possible to separate the material contribution from the thickness contribution and hence determine both, provided that we have a sufficient number of different filters in place.

If one placed individual filters in individual measurements this could be achieved but the multi-absorption plate allows for an effective filtering of the energy space simultaneously. This may be achieved using the spatial redundancy of a camera or by grouping together blocks of pixels. Alternatively, adjacent pixels may be interleaved preferably in both the x and y directions of the detector.

Hence, by introducing the multi-absorption plate it is possible to estimate accurately both the type and thickness of material through which an x-ray photon impinging on an area of an x-ray detector corresponding in size to the size of a particular region of the multi-absorption plate has passed.

Figure 2:
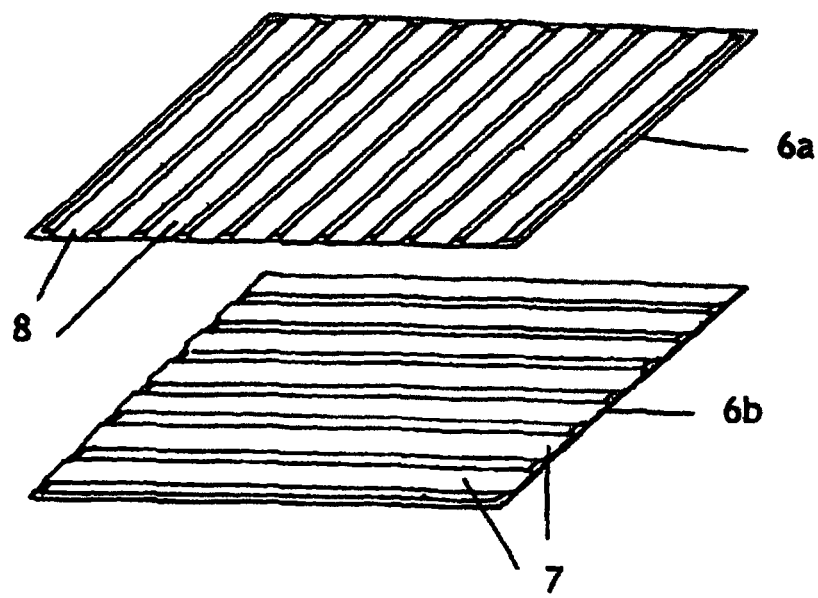
FIG. 2 is a schematic representation of components of a multi-absorption plate of the invention.

FIG. 2 illustrates the components of a multi-absorption plate 6. The multi-absorption plate 6 is comprised of two plates 6a, 6b each comprising a plurality of parallel and spaced apart strips of copper 6a' and 6b' respectively. The plates 6a, 6b are aligned perpendicular to one another and attached in this configuration. For example, the plates 6a, 6b may be attached to one another, by a resin, or each of the plates 6a, 6b may be mounted in a frame.

Figure 3:
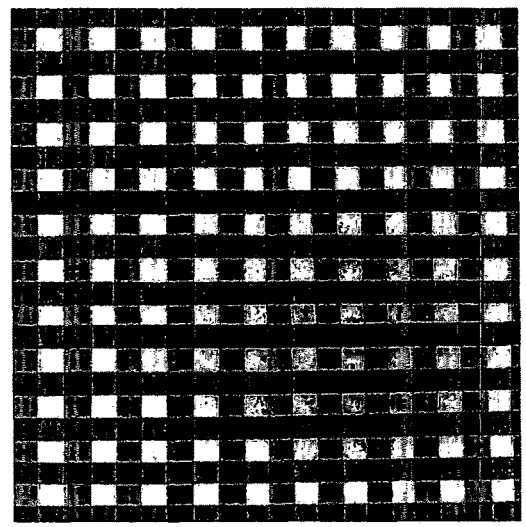
FIG. 3 is a schematic representation of a multi-absorption plate formed from the components illustrated in FIG. 2.

FIG. 3 illustrates the arrangement of the plates 6a, 6b of the multi-absorption plate 6. As can be seen, the plate 6 provides a repeating two by two matrix of regions 9-12, each providing a different degree of attenuation to an x-ray signal passing through the multi-absorption plate 6. In FIG. 3 four of the two by two arrays are outlined in a solid line simply to indicate the repeating structure within the multi-absorption plate 6.

The two by two array comprises a first region 9 formed by two layers of copper, one of a copper strip 8 of plate 6a and one of strip 7 of plate 6b. The second region 10 consists of a layer of copper formed by the copper strip 7 of plate 6b. The third region 11 is consists of a layer of copper formed by the copper strip 8 of plate 6a. The fourth region 12 does not include any copper and is formed by the spaces between the copper strips 7 and the spaces between copper strips 8. Hence the region 12 provides no attenuation.

It will be appreciated that the structure of the multi-absorption plate 6 will be imprinted on any image detected by the x-ray camera 3.

Figure 4:
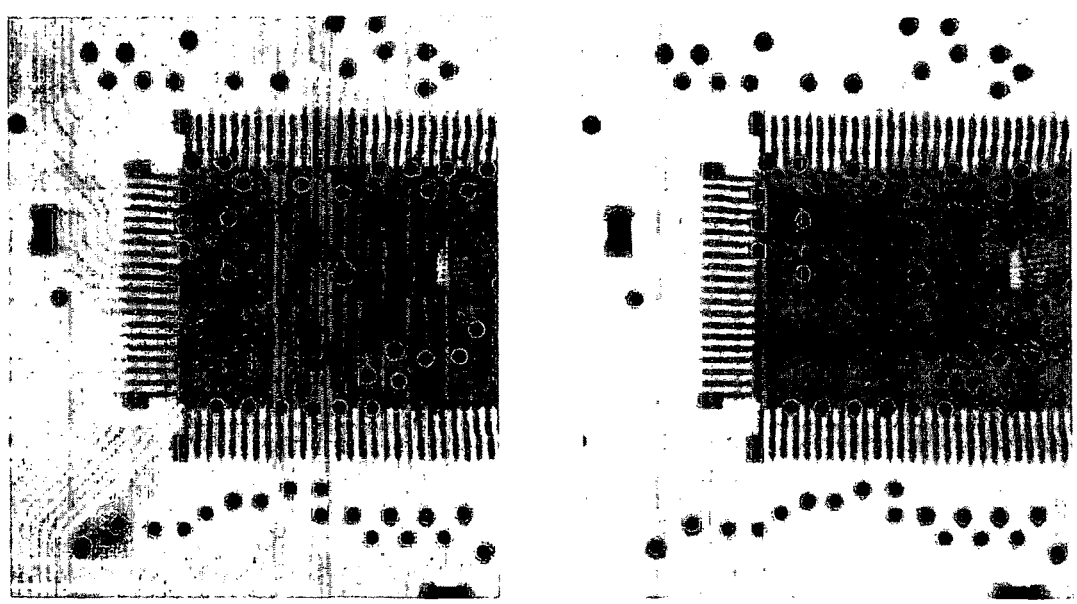
FIG. 4 shows two x-ray images one taken with an x-ray detector with a multi-absorption plate between the source and the object and the other without the multi-absorption plate.

FIG. 4 illustrates two x-ray images of a printed circuit board, the one on the left taken with a multi-absorption plate 6 of the type described above position between the x-ray source and the printed circuit board and the other to the right taken without the multi-absorption plate. Whilst the individual regions of the multi-absorption plate cannot be discerned, it is apparent that the contrast in the image on the right is greater than that on the left, i.e. the multi-absorption plate has hardened the x-ray energy spectrum.

However, by processing the data associated with each region of the multi-absorption plate 6 it is possible to counteract the effect of the plate 6. The effect of each region of the MAP 6 can be established by testing and the hardening effect added back to the signal recorded at each pixel associated with a group of the MAP.

Figure 6A:
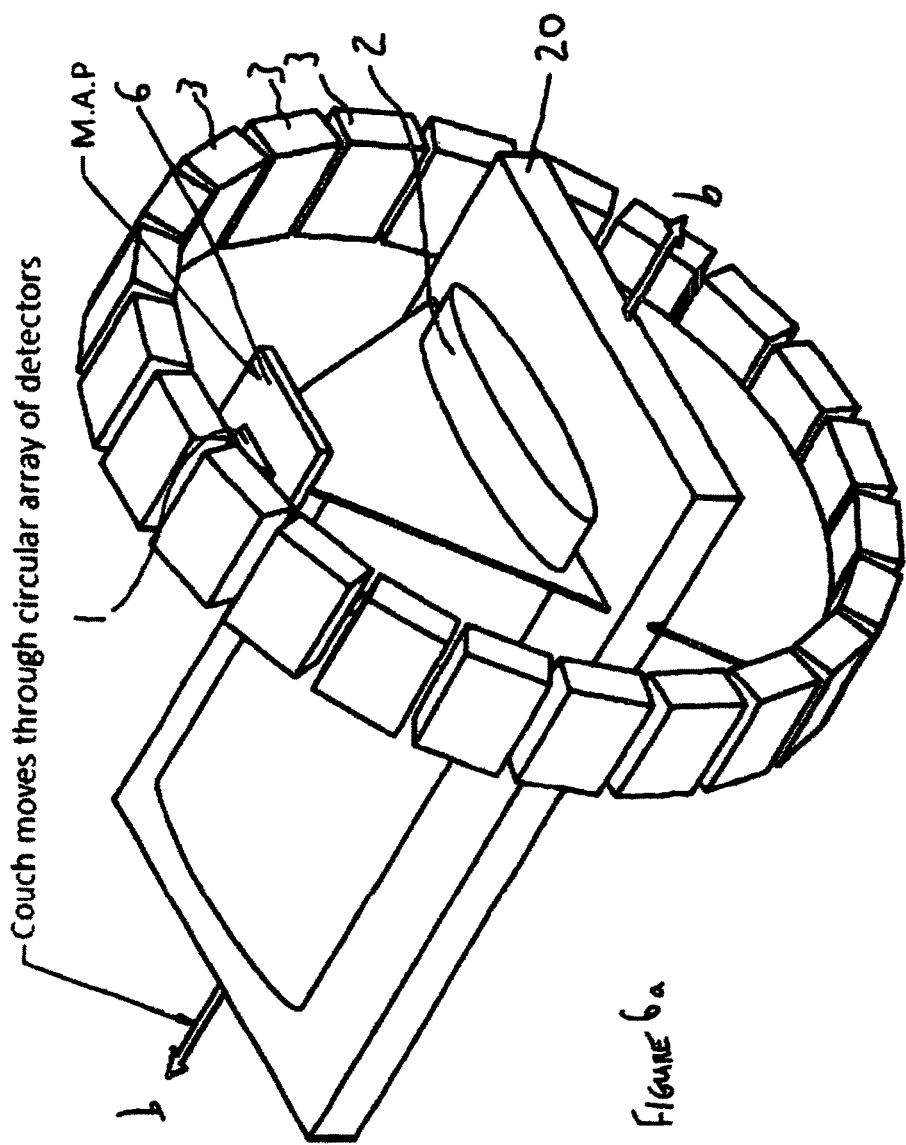
FIG. 6a is a schematic representation of a CT scanning x-ray apparatus according to the invention.

FIGS. 6a and 6b illustrate apparatus of the invention in the form of a computed tomography (CT) scanner which comprises a circular array of x-ray cameras 3 mounted to rotated around a patient support 20 in the direction indicated by arrow a. An x-ray source 1 is mounted above the patient support and arranged to direct an x-ray energy spectrum towards a patient 2 supported on the patient support 20. A multi-absorption plate 6 of the type shown in FIG. 3 is mounted between the x-ray source 1 and the patient 2. The patient support 20 is configured to translate in along the axis b-b so that the part of the body of the patient 2 of interest to a clinician may be scanned.

Figure 10:
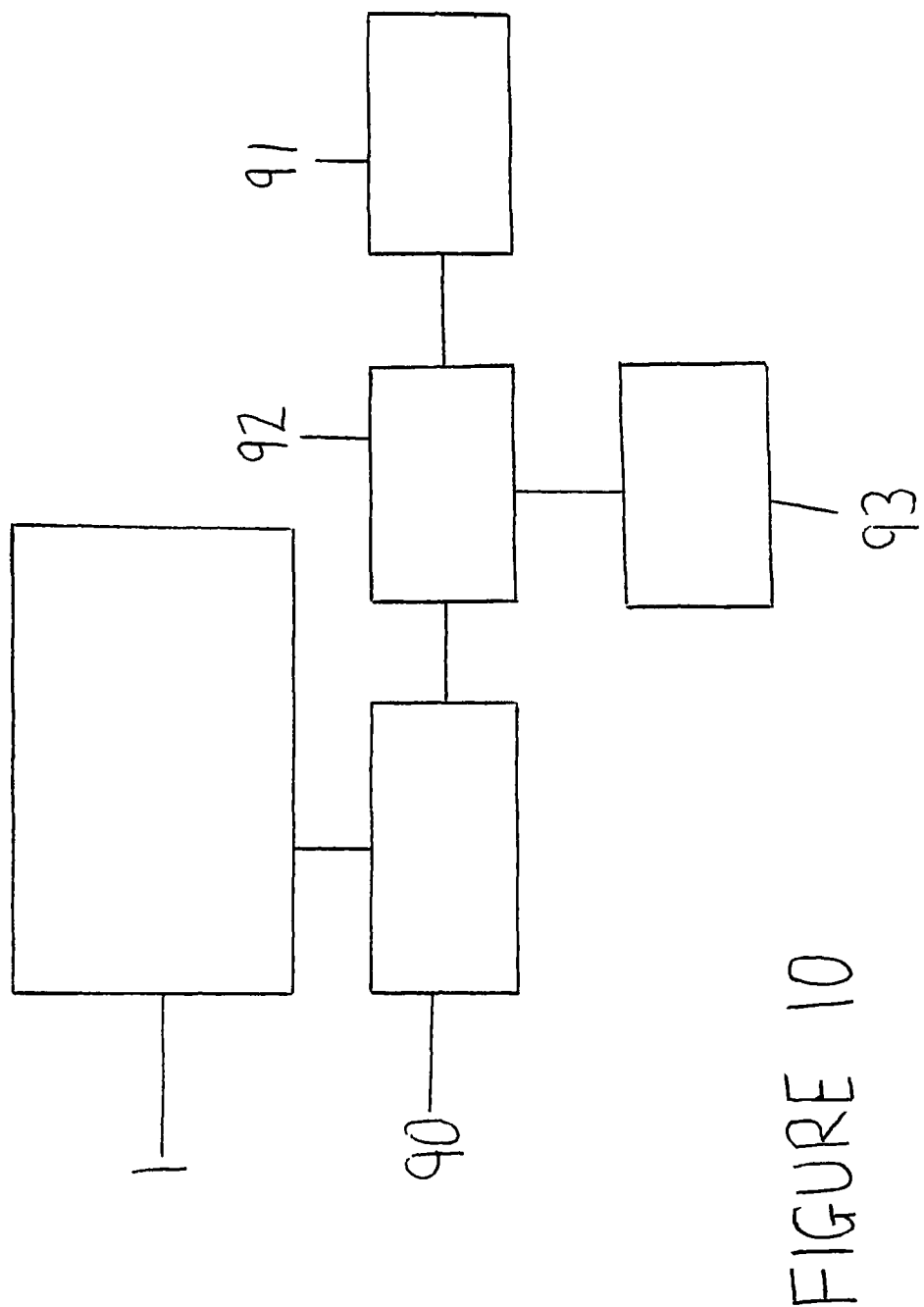
FIG. 10 is a block diagram of an embodiment of the invention.

FIG. 10 is a block diagram of a system according to an embodiment of the invention in which the detector 1 (which may one of the x-ray cameras 3 of the embodiment described with reference to FIGS. 6 and 6b or detector of any embodiment falling within the scope of the claims) provides an output to a data recording means 90. The data recording means is in communication with a data processor as is a database 91 in which data characteristic of known materials are recorded. The data recording means 90 and the database 91 are in communication with a data processor 92 which runs data processing software, the data processing software comparing information from the data from the detector, preferably via the recording means and the database to determine a material property of an object 3. A data output interface 93, such as but not limited to a VDU, is preferably included to which a determination of the data processing software may be outputted.

Analysis and Image Processing

FIG. 5 is a flow chart illustrating the operation of the x-ray detector of the invention.

The image collection phase of operation consists of taking an x-ray image using the apparatus illustrated in FIG. 1. The left hand image in FIG. 4 represents an output image in the image collection phase.

The analysis and image processing software performs both image analysis and image clean-up.

Using an exponential attenuation law based on the simplified version described above, the material through which the x-ray has passed and the thickness of that material can be estimated accurately. Image processing software calculates estimated values of material type and thickness for each region 8 to 12 of the multi-absorption plate 6.

The flow chart indicates that image analysis and clean-up occur concurrently but separately. These operations run as follows:

1) An FFT (fast fourier transform) is performed on the raw image to move it to the Fourier domain
2) the appropriate frequencies in the Fourier domain are masked (i.e. turn their intensity to zero in the Fourier image) to remove MAP and beam spot distortions from the image
3) An inverse FFT is performed to the modified Fourier Image to translate back to a standard image which has now been cleaned up.
4) The cleaned up image is segmented to produce regions of interest
5) The region map that is produced is then used to divide the original raw image into appropriate regions
6) For every region an appropriate thickness is estimated based on the average transmission for every material of interest
7) In each region of interest the pixels are also divided into the groups corresponding to which part of the MAP they correspond
8) Each pixel is then assessed against possible solutions in a database and mathematical methods are used, for example Bayesian analysis may be used, to assign probabilities of the matched solution being correct
9) The individual results of each region and each grouping of the MAP are then collated and the solution which is determined the most probable is selected and the material and thickness information is then coded for that particular region.
10) The same identification process is followed for every region of the image until all regions are identified.

For each region of the MAP, there will be representative pixels on the camera and the camera may have more pixels than the MAP has regions. These representative pixels are analysed relative to each other and the information used to help separate the degeneracy of thickness and material type as set out in steps 5 to 10 above. For instance, one region of the MAP may indicate that a particular material was silver of a particular thickness whereas the other areas of the MAP may indicate that it is tungsten of a particular thickness. Therefore the responses are all considered and the tungsten would be selected. It is possible to conclude the nature and thickness of a particular material because whilst material and thickness can be degenerate at one energy level they can't be degenerate at all energy levels.

More specifically, one method of determining material type and/or thickness follows a three step process post removal of the effect of the MAP from the recorded data.

In step 1 the actual intensities detected at individual pixels are grouped together and a intensity value is assigned to all pixels in that group;

In step 2, the assigned intensity value is compared with intensities recorded in the database and a number of possible solutions from the data base are identified;

In step 3, the averages of all the intensities of pixels associated with each different region of the structure are calculated for the group—note that this step is not dependent on having previously executed step 2;

In step 4, the differences between the averages of detected actual intensities related to different regions of the structure with the differences between the averages of actual intensities related to the same different regions of the structure in the database;

In step 5, the second and third moments of the transmission space of the detected intensities related to different regions of the structure are compared with the second and third moments of the transmission space for intensities stored in the database and related to the same different regions of the structure;

In step 6 a probability indicating that the body under test is the same as a known material type and/or thickness as stored in the database is issued.

The output of one step may form the input to a subsequent step so that the number of possible solutions reduces with each step. Alternatively, the steps may be performed independently of one another and the processed to find the result that best satisfies each step.

This multi-step process allows the number of possible solutions, that is material types and/or thicknesses, to be narrowed significantly so that in many cases an accurate probability may be issued. Where the probability does not give a great degree of certainty this may mean that the material is changing.

The apparatus may also be configured to associate certain material types and/or thicknesses with certain characteristics. For example, certain material types and/or thicknesses may indicate that a tissue is probably cancerous or probably not cancerous and the apparatus may be configured to issue an output indicating this. This could be useful in screening applications.

As stated above, the number of pixels in a modern x-ray camera is generally far greater than the minimum feature size within a sample object. Hence, there is spatial redundancy within the camera. This is used by assuming that the pixels are so finely spaced that adjacent pixels are likely looking at the same region of material. Therefore if adjacent pixels are altered by putting different filter materials in front of them then it can be assume the material in the object is the same in the adjacent pixels and so any change seen is due to the differences that are imposed by the MAP.

To determine a material property of a substance the substance is positioned on a sample stage and the x-ray source is caused to direct an x-ray energy spectrum through the multi-absorption plate, the so positioned sample to impinge upon the detector. Visible wavelength photons emitted by the member configured to convert incident x-ray wavelength photons into visible wavelength photons are then analysed according to the following steps:

Step (i)—The detector is pixellated: the intensity of visible wavelength photons recorded by the detector for each pixel is compared with the recorded intensity for its adjacent pixels and the differences in intensity are recorded with a substance present in the apparatus;

Step (ii)—The intensity of visible wavelength photons recorded by the detector for each pixel is compared with the recorded intensity for its adjacent pixels and the differences in intensity are recorded without a substance present in the apparatus;

Step (iv)—The current differences between recorded intensities between adjacent pixels as determined with by the method steps (i) and (ii) are compared;

Step (v)—Following the method steps (i) to (iv) for at least one known material and storing the differences in a database; and Step (vi)—Comparing the differences between recorded intensities for a substance under test with the differences between recorded intensities for known substances from the database.

In the case of human and veterinary medicine, a database of intensities representing the different types of tissue found in the body may be built up by testing biopsies, cadavers and/or parts of cadavers. In the case of human a animal tissue it is believed that this can be achieved with a moderate number of real measurements because there is only a limited number of different types of tissue in human and animal bodies.

Random noise reduction will now be described with reference to FIGS. 7 to 9. The reduction in random noise is carried out after the material type and/or thickness identification steps have been carried out.

FIG. 7 illustrates a theoretical image 50 comprising two regions 50a, 50b which represent a test material comprising two different materials and a liner MAP 60 comprising four regions 60a, 60b, 60c and 60d. The MAP 60 is aligned with the test material and an x-ray energy spectrum indicated by the dashed line 70 is caused to impinge upon the MAP 60 and the material under test. The graph shows the average intensity versus time detected by the detector. The graph shows two sets of steps a-d, each corresponding to a region 60a to 60d of the MAP 60, and each step of the two different sets being at a different average intensity. As discussed above, the actual intensity at any point in time is likely to differ from the average intensity, and because of the sensitivity of biological material to x-ray energy, much biological material can only be subjected to x-rays for very limited periods of time.

Figure 8:
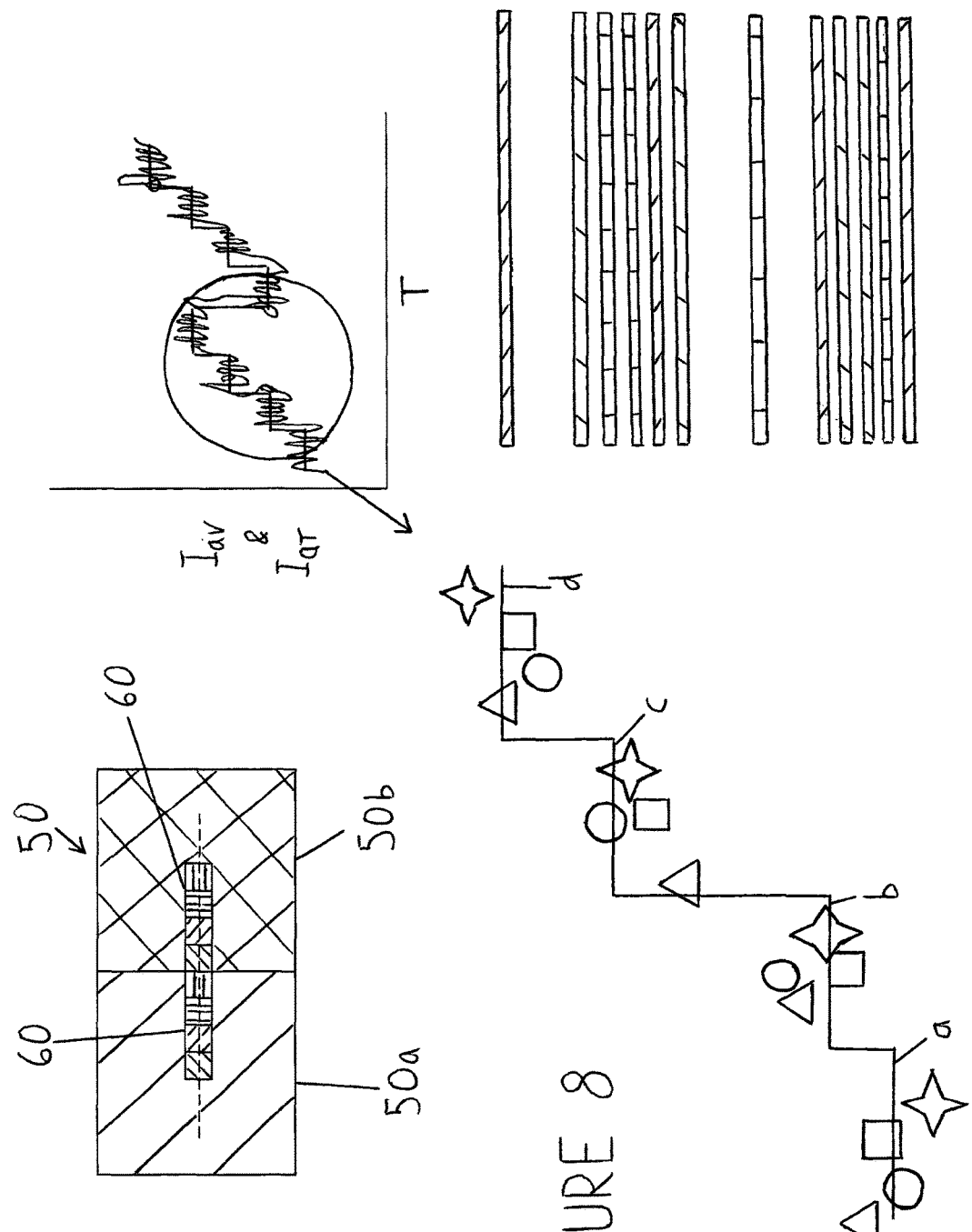
FIG. 8 illustrates components of the apparatus and graphs depicting the variation in actual detected intensity and the average.

In FIG. 8 the top right graph shows actual intensity is superposed over the average intensity in the graph of intensity versus time of FIG. 7. The deviation in intensity with respect to the average represents random noise. The bottom left graph highlights how this noise occurs. The four stars associated with each step a to d represent the intensity recorded in one of four detector pixels aligned with a respective one of the regions 60a to 60d. It can be seen that at each step the recorded intensity deviates from the average represented by the horizontal line of the step. Moreover, the deviation is not the same from step to step. This is because the arrival rate of photons in the detector is inconsistent from frame to frame. This phenomenon is well understood. What has not been understood is this random noise can be corrected for.

Figure 9:
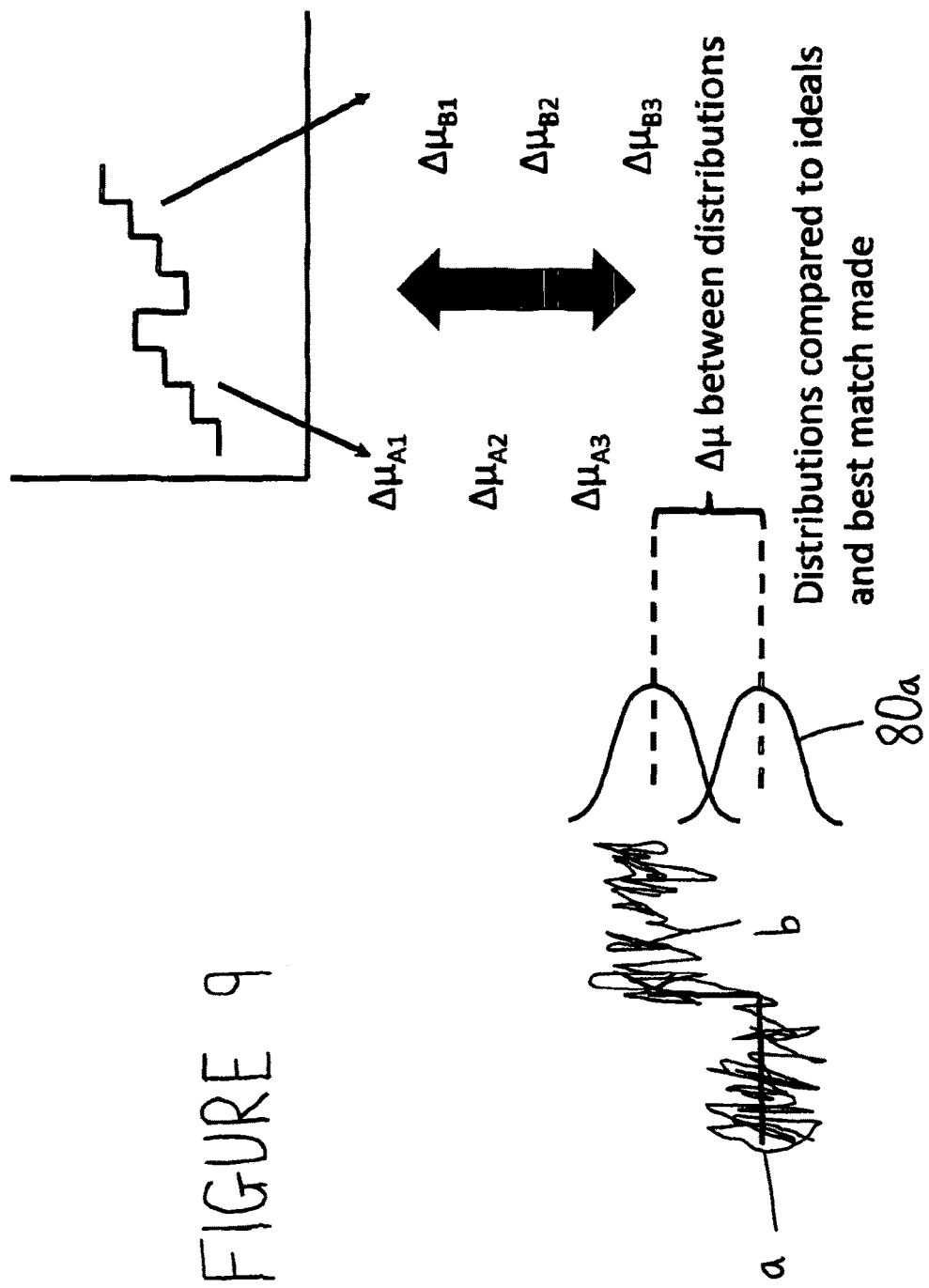
FIG. 9 illustrates the distributions of differences detected intensity.

FIG. 9 shows that there is a difference in intensity of $\Delta\mu$ between the average intensities associated with adjacent regions of the MAP 60, the differences being $\Delta\mu_{A1}$ $\Delta\mu_{A2}$, $\Delta\mu_{A3}$ and $\Delta\mu_{B1}$, $\Delta\mu_{B2}$, $\Delta\mu_{B3}$ for the respective regions 60a-60d.

FIG. 9 also shows the bell curves 80a, 80b representing the actual intensities associated with the steps a and b. The distance from peak to peak of the bell curves 80a, 80b represents $\Delta\mu_{A1}$. If random noise (and other sources of noise as discussed below) were eliminated the bell curves 80a, 80 would each become a single line lying on the centreline of each respective bell curve. $\Delta\mu_{A1}$, $\Delta\mu_{A2}$, $\Delta\mu_{A3}$ and $\Delta\mu_{B1}$, $\Delta A_{B2}$, $\Delta\mu_{B3}$ would remain the same.

The database can be used following more than one method. A first and preferred method uses the database to significantly reduce the random noise associated with the X-ray source by amending the actual x-ray intensities recorded by the detector. A second method involves reconstructing an image from the database. The advantage of the first method is that no data is lost, whereas in the second method data can be lost. For example, if the comparison with the database indicates that the best match for a particular region a certain material, in a reconstructed image the pixels associated with that particular region would represent the indicated material, whereas in reality one or more pixels representing a part of the region may have received a signal through a different material.

In the method where information stored in the database is used to reduce noise by amending the actual x-ray intensities, the intensities recorded at all pixels associated within a group of regions of the MAP (and the group may include all regions of the map) are compared with the database of intensities recorded for the same group of regions for different materials. The database may also include a record of intensities recorded for the same group of regions for the MAP itself. This latter record provides values of $\Delta\mu_{A1}$, $\Delta\mu_{A2}$, $\Delta\mu_{A3}$ for the MAP.

The step of comparing the recorded intensities with intensities in the database looks at the differences in recorded intensity in those pixels associated with adjacent regions of the MAP as compared with the differences between intensity in the pixels associated with the same types of adjacent regions of the MAP recorded in the database.

This information may be used in many different algorithms to apply a correction to the recorded intensities.

One approach is to amend the variance between pixel to pixel differences in the recorded intensities and pixel to pixel differences in the data base for the identified material by applying a scaling factor that suppresses the variance. In this way the differences in recorded intensities between adjacent pixels resemble more closely the differences ($\Delta\mu_{A1}$, $\Delta\mu_{A2}$, $\Delta\mu_{A3}$ a) in recorded intensities in the database. The scaling factor may be adjusted according to degree of certainty that the material represented by a group of pixels is the same material. For example, where the intensities recorded for many pixels of the detector are similar, there can be a high level of certainty that those pixels represent the same material. At the extreme, where certainty is very high, the recorded intensities may be amended so that the differences in intensity between pixels associated with adjacent regions of the MAP is the same as $\Delta\mu_{A1}$, $\Delta\mu_{A2}$, $\Delta\mu_{A3}$.

Where there is less certainty as to whether adjacent pixels represent the same material, the effect of noise may still be reduced but a different scaling factor that loses less information may be used.

The effect of this approach is to reduce the width of the bell curves in FIG. 9, at the extreme reducing the bell curve to a straight line.

A less sophisticated approach would be to apply a common scaling factor to the recorded intensities at all pixels rather than applying different scaling factors depending on the level of confidence in certain groups of pixels representing the same material.

When recorded intensities are compared with intensities representative of materials in the database Bayesian statistics and/or Gaussian processes may be used to assign recorded intensities to a particular material, that is to say that when a material is under test, for example an x-ray image is being taken of a person's hand, the intensities recorded at each pixel in the step of comparing the recorded intensities with the information stored in the database to identify which material identity is most closely resembled by the recorded intensities Bayesian statistics and/or Gaussian processes may be used.

In this specification the terms "intensity" and "transmission" are used. Intensity and transmission are related, the detected transmission (also representing the percentage transmission) being the normalised intensity.

The present invention is particularly effective at reducing random noise associated with fluctuation in the arrival rate of photons at the detector. However, there are other noise influences that affect x-ray equipment in addition to random noise associated with fluctuation in the arrival rate of photons at the detector. These other noise contributions are known and methods for correcting for them are also known. However, the apparatus, methods and processes of the invention have be found to be very effective in reducing systemic noise.

The apparatus and method of the invention provide for significantly reduced x-ray dose, which is of significant advantage when taking images of anything susceptible to damage by x-rays or other ionising radiation.

The invention claimed is:

1. An x-ray/gamma ray imaging apparatus, the apparatus including a pixilated x-ray/gamma ray detector comprising a detector member configured to detect incident x-ray/gamma ray wavelength photons a position for a body under test, an x-ray or gamma ray source, and a structure configured to perturb the energy spectrum, each lying on a common axis, wherein the source is arranged to direct an x-ray/gamma ray energy spectrum along the common axis to impinge upon the structure configured to perturb the x-ray energy spectrum, and a positioned body/object under test, wherein said structure and the position for the body under test lie between the source and the detector member wherein the said structure comprises at least three adjacent regions, each region different to immediately adjacent regions and configured to perturb the x-ray energy spectrum differently, wherein the difference between adjacent regions includes at least one of: thicknesses of material forming adjacent regions; the presence of material forming adjacent regions; and the type of material forming adjacent regions, the apparatus further comprising image processing software and a database, wherein the database stores information indicative of at least one of: material type; material thickness; and material type and thickness, said information related to the effect of an x-ray/gamma ray energy spectrum of a similar source on a combination of the structure and the at least one material over period of time sufficient to allow the centre of fluctuation of the x-ray/gamma ray energy spectrum to be ascertained, wherein the structure comprises repeating arrays each array comprising the at least three adjacent regions, each region different to immediately adjacent regions and configured to perturb the x-ray energy spectrum differently, and wherein the image processing software is configured to execute a materials identification algorithm to determine a selected one of: the material type; the material thickness; and the material type and thickness of the body through which the x-ray wavelength photons have passed, and wherein the image processing software compares outputs of pixels of the detector with information stored in the database and processes the outputs of the detector according to a noise reduction algorithm that uses information from the database.

2. An x-ray imaging apparatus according to claim 1, wherein the said structure lies between the x-ray source and the position for the body under test each intersecting the common axis.

3. An x-ray imaging apparatus according to claim 1, wherein the said structure lies between the position for the body under test and the detector each intersecting the common axis.

4. An x-ray imaging apparatus according to claim 1, wherein one of the regions is an aperture.

5. An x-ray imaging apparatus according to claim 1, further including a collimator configured to collimate x-ray wavelength photons emitted by the x-ray source.

6. An x-ray imaging apparatus according to claim 5, wherein each array of the structure of repeating arrays is aligned with a beam of x-ray energy produced by the collimator.

7. An x-ray imaging apparatus according to claim 1, wherein the number of pixels in the detector member is greater than or equal to the number of regions in the structure.

8. An x-ray imaging apparatus according to claim 1, further comprising data recording means configured to record the detected incident x-ray/gamma ray wavelength photons for a selected one of: individual pixels and groups of pixels.

9. An x-ray imaging apparatus according to claim 8, wherein differences between the outputs of pixels of the detector and information stored in the database are recorded in the data recording means.

10. An x-ray imaging apparatus according to claim 1, wherein image processing software is configured to remove the effect of the structure on the detected x-ray/gamma ray photons.

11. An x-ray imaging apparatus according to claim 1, wherein the noise reduction algorithm compares the difference in outputs of adjacent pixels of the detector with differences between outputs of adjacent pixels for identified database entries and amends the outputs of the adjacent pixels of the detector such that the differences in those outputs resembles more closely the differences between outputs of adjacent pixels for identified database entries that are similar to the outputs of adjacent pixels of the detector.

12. An x-ray imaging apparatus according to claim 11, wherein image processing software is configured such that amendment of the outputs of pixels in a group of pixels associated with a region of the structure is common to the output of each pixel in the group.

13. An x-ray imaging apparatus according to claim 11, wherein the image processing software is configured such that the extent to which the outputs are amended to resemble more closely the difference between outputs of adjacent pixels for the identified database entries that are similar to the outputs of adjacent pixels of the detector is controllable.

14. An x-ray imaging apparatus according to claim 13, wherein the image processing software is configured to select the extent of amendment according to the degree of certainty that a group of pixels represent the same material, and wherein the greater the certainty, the greater the amendment of the outputs adjacent pixels of the detector may be.

15. An x-ray imaging apparatus according to claim 1, wherein the noise reduction algorithm identifies information in the database that most closely resembles outputs of pixels of the detectors and replaces the outputs of pixels with the identified information in the database.

16. An x-ray imaging apparatus according to claim 15, wherein the outputs of pixels in a group of pixels associated with a region of the structure are replaced with the same identified information.

17. An x-ray imaging apparatus according to claim 10, wherein the image processing software is configured to provide an output of a characteristic associated with the detection of a selected one of: a certain material type; a certain material thickness; and a certain material type and thickness.

18. A medical device comprising x-ray imaging apparatus according to claim 1, wherein the position for a body under test is a patient support.

19. A medical device according to claim 18, comprising a plurality of detectors.

20. A medical device according to claim 19, wherein the plurality of detectors is mounted for rotation about the patient support.

21. An image analysis process comprising the steps of: detecting x-ray signals using an x-ray imaging apparatus including a pixilated x-ray/gamma ray detector comprising a detector member configured to detect incident x-ray/gamma ray wavelength photons a position for a body under test, an x-ray or gamma ray source, and a structure configured to perturb the energy spectrum, each lying on a common axis, wherein the source is arranged to direct an x-ray/gamma ray energy spectrum along the common axis to impinge upon the structure configured to perturb the x-ray energy spectrum, and a positioned body/object under test, wherein said structure and the position for the body under test lie between the source and the detector member wherein the said structure comprises at least three adjacent regions, each region different to immediately adjacent regions and configured to perturb the x-ray energy spectrum differently, wherein the difference between adjacent regions includes at least one of: thicknesses of material forming adjacent regions; the presence of material forming adjacent regions; and the type of material forming adjacent regions, the apparatus further comprising image processing software and a database, wherein the database stores information indicative of at least one of: material type; material thickness; and material type and thickness, said information related to the effect of an x-ray/gamma ray energy spectrum of a similar source on a combination of the structure and the at least one material over period of time sufficient to allow the centre of fluctuation of the x-ray/gamma ray energy spectrum to be ascertained, wherein the structure comprises repeating arrays each array comprising the at least three adjacent regions, each region different to immediately adjacent regions and configured to perturb the x-ray energy spectrum differently, and wherein the image processing software is configured to execute a materials identification algorithm to determine a selected one of: the material type; the material thickness; and the material type and thickness of the body through which the x-ray wavelength photons have passed, and wherein the image processing software compares outputs of pixels of the detector with information stored in the database and processes the outputs of the detector according to a noise reduction algorithm that uses information from the database;

associating pixels of the detector with regions of the structure;

removing noise from the detected signals using mathematical methods utilizing a priori information contained in the image and associated with the different regions of the structure that is matched to information in the database.

22. An image analysis process according to claim 21, comprising the step of recording the detected incident x-ray/gamma ray wavelength photons for a selected one of: individual pixels; groups of pixels; and individual and groups of pixels, in the data recording means.

23. An image analysis process according to claim 21, comprising the step of removing the effect of the structure on the detected x-ray/gamma ray photons.

24. An image analysis process according to claim 21, including the step of grouping together pixels having similar outputs.

25. An image analysis process according to claim 24, the comprising the step of assigning the same output to all pixels in a group of pixels.

26. An image analysis process according to claim 21, comprising the step of recording differences between the outputs of pixels of the detector and information stored in the database in the data recording means.

27. An image analysis process according to claim 21, wherein the step of executing the materials identification algorithm includes comparing the actual intensity detected at a pixel or assigned to a group of pixels with actual intensities recorded in the database.

28. An image analysis process according to claim 27, wherein the materials identification algorithm comprises the further step of comparing differences between the averages of detected actual intensities related to different regions of the structure with the differences between the averages of actual intensities related to the same different regions of the structure in the database.

29. An image analysis process according to claim 27, wherein the algorithm comprises the further step of comparing the second and third moments of the transmission space of the detected intensities related to different regions of the structure with the second and third moments of the transmission space for intensities stored in the database and related to the same different regions of the structure.

30. An image analysis process according to claim 27, wherein the algorithm includes the further step of issuing a probability indicating that the body under test is the same as one of: a known material type; a known material thickness; and a known material type and thickness as stored in the database.

31. An image analysis process according to claim 21, wherein the image processing software executes the noise reduction algorithm.

32. An image analysis process according to claim 31, wherein the noise reduction algorithm is configured to suppress the variance in pixel to pixel differences in the actual detected intensity and pixel to pixel differences in the database for the identified material.

33. An image analysis process according to claim 32, wherein the algorithm includes the further step of issuing a probability indicating that the body under test is the same as one of: a known material type; a known material thickness; and a known material type and thickness as stored in the database and wherein the degree of variance suppression is controlled in relation to the issued probability of the body under test being a known material type and/or thickness and wherein greater the probability the greater the suppression of the variance.

34. An image analysis process according to claim 21, wherein the noise reduction algorithm compares the difference in outputs of adjacent pixels of the detector with differences between outputs of adjacent pixels in the database and amends the outputs of the adjacent pixels of the detector such that the differences in those outputs resembles more closely the differences between outputs of adjacent pixels in the database.

35. An image analysis process according to claim 34, wherein image processing software makes a common amendment to the outputs of pixels in a group of pixels associated with a region of the structure.

36. An image analysis process according to claim 34, wherein the image processing software controls the extent to which the outputs are amended to resemble more closely the difference between outputs of adjacent pixels in the database.

37. An image analysis process according to claim 36, comprising the step of controlling the extent of amendment according to the degree of certainty that a group of pixels represent the same material, and wherein the greater the certainty, the greater the amendment of the outputs adjacent pixels of the detector may be.

38. An image analysis process according to claim 21, wherein the noise reduction algorithm identifies information in the database that most closely resembles outputs of pixels of the detectors and replaces the outputs of pixels with the identified information in the database.

39. An image analysis process according to claim 38, comprising the step of replacing the outputs of pixels in a group of pixels associated with a region of the structure with the same identified information.

40. An image analysis process according to claim 27, comprising the additional step of providing an output indicating the probability of one or more characteristics being associated with the identified the material type and/or material thickness.

41. An image analysis process according to claim 40, wherein the characteristic is indicative of a medical condition.

* * * * *